United States Patent
Karussis et al.

(10) Patent No.: US 10,336,985 B2
(45) Date of Patent: Jul. 2, 2019

(54) METHOD OF OBTAINING TERMINALLY DIFFERENTIATED NEURONAL LINEAGES AND USES THEREOF

(71) Applicant: Hadasit Medical Research Services & Development Limited, Jerusalem (IL)

(72) Inventors: Dimitrios Karussis, Jerusalem (IL); Ibrahim Kassis, Abu Gush (IL)

(73) Assignee: Hadasit Medical Research Services & Development Limited, Jerusalem (IL)

( * ) Notice: Subject to any disclaimer, the term of this patent is extended or adjusted under 35 U.S.C. 154(b) by 0 days.

(21) Appl. No.: 15/029,127

(22) PCT Filed: Oct. 7, 2014

(86) PCT No.: PCT/IL2014/050884
§ 371 (c)(1),
(2) Date: Apr. 13, 2016

(87) PCT Pub. No.: WO2015/056258
PCT Pub. Date: Apr. 23, 2015

(65) Prior Publication Data
US 2016/0251619 A1  Sep. 1, 2016

Related U.S. Application Data

(60) Provisional application No. 61/890,481, filed on Oct. 14, 2013.

(51) Int. Cl.
*C12N 5/079* (2010.01)
*A61K 35/28* (2015.01)
*C12N 5/0793* (2010.01)

(52) U.S. Cl.
CPC ............ *C12N 5/0622* (2013.01); *A61K 35/28* (2013.01); *C12N 5/0618* (2013.01); *C12N 5/0619* (2013.01); *C12N 2500/84* (2013.01); *C12N 2501/11* (2013.01); *C12N 2506/1353* (2013.01)

(58) Field of Classification Search
CPC ............ C12N 5/0618; C12N 2500/84; C12N 2501/11; C12N 2506/1353; C12N 5/0619; C12N 5/0622; A61K 35/28
See application file for complete search history.

(56) References Cited

U.S. PATENT DOCUMENTS

| | | | |
|---|---|---|---|
| 2008/0176328 A1 | 7/2008 | Chang et al. | |
| 2009/0162327 A1* | 6/2009 | Li | A61K 35/28 424/93.7 |
| 2013/0202565 A1 | 8/2013 | Park et al. | |

FOREIGN PATENT DOCUMENTS

| | | |
|---|---|---|
| CN | 101245336 A | 8/2008 |
| CN | 103031275 A | 4/2013 |
| WO | 2004/046348 A1 | 6/2004 |
| WO | 2006/134602 A2 | 12/2006 |
| WO | 2007/066338 A1 | 6/2007 |
| WO | 2007/136156 A1 | 11/2007 |
| WO | 2008/057443 A2 | 5/2008 |
| WO | 2009/144718 A1 | 12/2009 |

OTHER PUBLICATIONS

Nagai A. et al., "Multilineage Potential of Stable Human Mesenchymal Stem Cell Line Derived from Fetal Marrow", PLoS ONE 2007, vol. 2, issue 12: e1272 (total pp. 1-18). (Year: 2007).*
Buddensiek et al., "Cerebrospinal fluid promotes survival and astroglial differentiation of adult human neural progenitor cells but inhibits proliferation and neuronal differentiation", BMC Neuroscience, vol. 11, p. 48, 11 pages, (2010).
Cao et al., "Autologous transplantation of bone marrow mesenchymal cells-derived neural stem cells for treating seven patients with central nervous system diseases", Journal of Clinical Rehabilitative Tissue Engineering Research, vol. 15, No. 1, pp. 163-166, (2011).
Chung et al., "A Comparison of Neurosphere Differentiation Potential of Canine Bone Marrow-Derived Mesenchymal Stem Cells and Adipose-Derived Mesenchymal Stem Cells", J. Vet. Med. Sci., vol. 75, No. 7, pp. 879-886, (2013).
Feng et al., "Secretion of nerve growth factor, brain-derived neurotrophic factor, and glial cell-line derived neurotrophic factor in co-culture of four cell types in cerebrospinal fluid-containing medium", Neural Regen Res. vol. 7, No. 36, pp. 2907-2914, (2012).

(Continued)

*Primary Examiner* — Satyendra K Singh
(74) *Attorney, Agent, or Firm* — Vorys, Sater, Seymour and Pease LLP

(57) ABSTRACT

Provided is a method of inducing transdifferentiation of mesenchymal stem cells (MSC), the method including (a) culturing MSC in a first culture medium including a growth factor selected for allowing formation of neuralized MSC (NMSC); (b) allowing the NMSC to proliferate for a sufficient time during which said culture medium is renewed at least once; and (c) culturing the NMSC of (b) in a second culture media including cerebrospinal fluid (CSF) for a time sufficient for the NMSC to differentiate into a population of cells including terminally differentiated neurons, astrocytes and oligodendrocytes. Also provided by the present invention is the use of MSC or NMSC for providing a composition including said population and to kits including MSC or NMSC and instructions for use of same.

13 Claims, 7 Drawing Sheets

(56) References Cited

OTHER PUBLICATIONS

González et al., "The CSF of normal H-Tx rats promotes neuronal differentiation from neurospheres but CSF of hydrocephalic H-Tx rats does not", Cerebrospinal Fluid Research, vol. 3, Suppl I, S10, 1 page, (2006).

Harris et al., "Clinical and pathological effects of intrathecal injection of mesenchymal stem cell-derived neural progenitors in an experimental model of multiple sclerosis", Journal of the Neurological Sciences, vol. 313, pp. 167-177, (2012).

Harris et al., "Characterization of Autologous Mesenchymal Stem Cell-Derived Neural Progenitors as a Feasible Source of Stem Cells for Central Nervous System Applications in Multiple Sclerosis", Stem Cell Translational Medicine, vol. 1, pp. 536-547, (2012).

Kim et al., "Neural differentiation potential of peripheral blood- and bone-marrow-derived precursor cells", Brain Research, vol. 1123, No. 1, pp. 27-33, (2006).

Pittenger et al., "Multilineage Potential of Adult Human Mesenchymal Stem Cells", Science, vol. 284, Issue 5411, pp. 143-147, (1999).

Radtke et al., "Peripheral glial cell differentiation from neurospheres derived from adipose mesenchymal stem cells", Int. J. Devl Neuroscience, vol. 27, pp. 817-823, (2009).

Sanchez-Ramos et al., "Adult Bone Marrow Stromal Cells Differentiate into Neural Cells in Vitro", Experimental Neurology, vol. 164, pp. 247-256, (2000).

Suzuki et al., "Neurospheres induced from bone marrow stromal cells are multipotent for differentiation into neuron, astrocyte, and oligodendrocyte phenotypes", Biochemical and Biophysical Research Communications, vol. 322, pp. 918-922, (2004).

Ye et al., "Induction of Human Bone Marrow Mesenchymal Stem Cells Differentiation into Neural-Like Cells Using Cerebrospinal Fluid", Cell Biochem Biophys, vol. 59, pp. 179-184, (2011).

Yang et al., "A simple and efficient method for deriving neurospheres from bone marrow stromal cells", Biochemical and Biophysical Research Communications, 372 (2008) 520-524.

\* cited by examiner

METHOD OF OBTAINING TERMINALLY DIFFERENTIATED NEURONAL LINEAGES AND USES THEREOF

TECHNOLOGICAL FIELD

The present disclosure concerns stem cells manipulation and in particular the manipulation of mesenchymal stem cells into neuronal lineages.

PRIOR ART

References considered to be relevant as background to the presently disclosed subject matter are listed below:

Pittenger M F, Mackay A M, Beck S C et al. "*Multilineage potential of adult human mesenchymal stem cells*". Science, 284(5411), 143-147 (1999).

Gonzales C, Vío K, Muñoz R I and Rodriguez E M "*The CSF of normal H-Tx rats promotes neuronal differentiation from neurospheres but CSF of hydrocephalic H-Tx rats does not*" Cerebrospinal Fluid Res. 3(Suppl 1): S10. (2006)

Judith Buddensiek, Alexander Dressel, Michael Kowalski, Uwe Runge, Henry Schroeder, Andreas Hermann, Matthias Kirsch, Alexander Storch, Michael Sabolek *Cerebrospinal fluid promotes survival and astroglial differentiation of adult human neural progenitor cells but inhibits proliferation and neuronal differentiation* Neuroscience 11:48 (2010)

Harris V K, Yan Q J, Vyshkina T, Sahabi S, Liu X, Sadiq S A. *Clinical and pathological effects of intrathecal injection of mesenchymal stem cell-derived neural progenitors in an experimental model of multiple sclerosis*. J Neurol Sci, 313(1-2), 167-177 (2012) #1.

Harris V K, Faroqui R, Vyshkina T, Sadiq S A. *Characterization of autologous mesenchymal stem cell-derived neural progenitors as a feasiable source of stem cells for central nervous system applications in multiple sclerosis*. Stem Cells Dev, 1(7), 536-547 (2012) #2.

Ying Ye, Yin-Ming Zeng, Mei Rong Wan, Xian Fu Lu "*Induction Of Human Bone Marrow Mesenchymal Stem Cells Differentiation Into Neural-Like Cells Using Cerebrospinal Fluid*" Cell Biochem biophys 59:179-184 (2011).

Radtke et al. "*Peripheral glial cell differentiation from neurospheres derived from adipose mesenchymal stem cells*", Int. J. Devl Neuroscience, 27:817-823 (2009).

Acknowledgement of the above references herein is not to be inferred as meaning that these are in any way relevant to the patentability of the presently disclosed subject matter.

BACKGROUND

MSCs are an important member of the bone marrow stem cell repertoire. These cells are described as nonhematopoietic stromal cells and their classical role is to support the process of hematopoiesis and HSC engraftement and to give rise to cells of mesodermal origin, such as osteoblasts, adipocytes and chondrocytes [Pittenger M F et al. 1999].

Various studies have depicted roles of MSCs, among others, their ability to transdifferentiate into cells of endodermal and ectodermal origin, including possible neural transdifferentiation and broad immunomodulating properties. In one publication it was shown that cerebrospinal fluid (CSF) of normal H-Tx rats promotes neuronal and glial differentiation from neurospheres and that the CSF from hydrocephalic H-Tx rats interferes with neuronal differentiation (Gonzales et. al. 2006). Another publication reported that CSF can promote survival and astroglial differentiation of adult human neural progenitor cells but inhibits proliferation and neuronal differentiation (Buddensiek et al. 2010)

There are recent reports that multiple intrathecal injections of mouse derived MSC neural progenitors (MSC-NPs) in an experimental model of multiple sclerosis (Harris V K et al. (2012) #1) induced a strong beneficial clinical effect on EAE. In another recent study by the same group, neurosphere-like cells were generated from multiple sclerosis patients and healthy donors (Harris V K et al. (2012) #2]. The investigators reported that multiple injections of MSC-NPs are advantageous as compared to a single injection and they improve the clinical and pathological parameters of EAE, and promote endogenous repair mechanisms.

The publications WO 2004/046348, WO 2006/134602, WO 2007/066338, WO 2009/144718 describe methods of neuronal differentiation.

Radtke et al (2009) describes the formation of neurospheres from adipose-derived stem cells and their differentiation in culture to peripheral glial-like cells.

In yet another study it was reported that CSF from healthy human donors can induce human bone marrow MSC to differentiate into neural-like cells (Ying Ye et al. (2011)).

GENERAL DESCRIPTION

The present disclosure provides a method of inducing transdifferentiation of mesenchymal stem cells (MSCs), the method comprising: (a) culturing MSCs in a first culture medium comprising a growth factor selected to allow formation of neuralized MSCs (NMSC); (b) allowing the NMSC to proliferate for a sufficient time during which the culture medium is renewed at least once; and (c) culturing the NMSC in a second culture media comprising cerebrospinal fluid (CSF) for a time sufficient for the NMSC to differentiate into a population of cells comprising terminally differentiated neurons, astrocytes and oligodendrocytes.

The present disclosure also provides the use of MSC for the preparation of a composition comprising a population of cells comprising terminally differentiated neurons, astrocytes and oligodendrocytes.

Within this aspect, the present disclosure also provides the use of neutralized mesenchymal stem cells (NMSC) for the preparation of a population of cells comprising terminally differentiated neurons, astrocytes and oligodendrocytes.

Also provided by the present disclosure is a kit comprising a composition comprising mesanchymal stem cells (MSC) and instructions for use of the MSC in a method of preparing a population of cells comprising terminally differentiated neurons, astrocytes and oligodendrocytes, the method being as defined herein.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIG. 1A show example of human MSC isolated from MS patients (passage 1) having fibroblast-like spindle shape morphology, FIGS. 1B and 1C show that after culturing MSC with neurosphere generation media for 5 days, floating NMSC having neurosphere-like structures emerged in culture (FIG. 1B—big window=×20 magnification, bar=100 μm; small window=×40 magnification of the spheres, bar=50 μm); FIG. 1C shows staining for the nuclei of the cells forming the spheres is demonstrated using the DAPI staining (bar 50 μm).

FIGS. 2A and 2B are image showing that NMSC generated from hMSC were positively stained for the marker Nestin (FIG. 2A) and PS-NCAM (FIG. 2B); FIG. 2C is a merged micrograph of the two markers measured in FIGS. 2A and 2B, FIG. 2D shows a representative FACS analysis of hMSC and NMSC showing that hMSC stained positively for the mesodermal markers CD90 and CD105 while being negative for the hematopoietic markers CD34 and CD45, whereas NMSC were stained positively for Nestin and PSNCAM while showing low to negative staining for the mesenchymal and hematopoietic markers CD34, CD45, CD90 and CD105.

FIGS. 4A-4D show neuronal differentiation of NMSC; NMSC seeded on Poly-L-Lysine coated culture wells (from the second week of culture) were cultured with 0.2% allogenic CSF (of MS patient), morphological changes were observed within the culture resembling neural and glial-like cells, a positive staining of the differentiated cells was observed for the neuronal marker MAP2 (FIG. 4A), a neuronal marker Class III β-tubulin (FIG. 4B), the astrocytic marker GFAP (FIG. 4C) and for the oligodendrocytic marker CNPase (FIG. 4D), bar=100 μm. FIG. 4E is an image of an astrocytes isolated from the brain (prior art); FIGS. 4F-4J show MSC cultured with allogenic CSF, the cells were grown and treated by the method described in Ye et al. FIGS. 4F-4G show immunohistochemistry staining with GFAP (FIG. 4F), Class III tubulin (FIG. 4G); FIGS. 4H-4J show immunofluorescence staining with GFAP (FIG. 4H), Class III tubulin (FIG. 4I), and the merging of the two markers (FIG. 4J).

DETAILED DESCRIPTION OF EMBODIMENTS

Figures 1A, 1B, 1C:
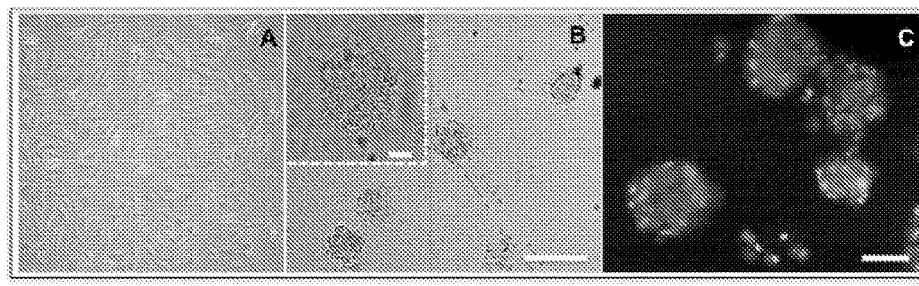
FIGS. 1A-1C are images showing generation of neuralized mesenchymal stem cells-neurospheres (NMSC) from MSC.

Neurodegenerative disorders such as multiple sclerosis, alzheimer's disease, parkinson's disease and huntington's disease involve the death of neurons in the brain. The same is true also for spinal cord injuries. Treatment of such diseases is currently limited and thus, there is a need fro alternative therapies. One approach involves the providence of transplantable cells produced for example from stem cells which may be used to replace the inactive neurons.

As shown herein the inventors have developed a novel method for generating of terminally differentiated neuronal cells from human bone marrow-derived mesenchymal stem cells (MSCs) via the establishment of intermediate neurospheres as discussed below.

Specifically, the inventors have found that neurospheres obtained from culturing MSC in the presence of growth factors resemble (in terms of same morphology and markers) neurospheres generated from adult neural stem cells (these neurospheres are thus being regarded as neuralized mesenchymal stem cells (NMSC)). These NMSC were found to be stable, i.e. maintained their morphology and expressed markers through subsequent proliferation stages.

Further, it was shown by the inventors that treatment of these stable NMSC with cerebrospinal fluid (CSF) allowed the NMSC to differentiate into all three cell types of the ectoderm lineage, namely, astrocytes, neurons and oligodendrocytes, as exhibited by their specific markers (see Table 2 below).

The differentiation induced by CSF was cell specific and the NMSC lost their potential to differentiate into cells of a mesodermal lineage.

Thus, in accordance with its first aspect, the present disclosure provides a method of inducing transdifferentiation of mesenchymal stem cells (MSCs), the method comprising:
(a) culturing MSCs in a first culture medium comprising a growth factor selected for allowing formation of neutralized MSCs (NMSC);
(b) allowing the NMSC to proliferate for a sufficient time during which said culture medium is renewed at least once;
(c) culturing the NMSC in a second culture media comprising cerebrospinal fluid (CSF) for a time sufficient for the NMSC to differentiate into a population of cells comprising terminally differentiated neurons, astrocytes and oligodendrocytes.

The above steps are conducted under commonly acceptable incubator conditions that maintains optimal temperature (e.g. approximately 37° C.), humidity (typically >95%) and other conditions such as the carbon dioxide ($CO_2$, typically 5%) and oxygen content of the atmosphere inside the incubator with periodical refreshing (replace and replenish) of the various culture media.

As used herein, the term "differentiation" refers to a process by which a less specialized cell becomes a more specialized cell type. Differentiation is a common process where, for example, stem cells divide and create partially or fully differentiated daughter cells, e.g. during tissue repair and during normal cell turnover. Differentiation dramatically changes a cell's size, shape, membrane potential, metabolic activity, and responsiveness to signals.

Further, as used herein, the term "transdifferentiation" denotes a process that takes place when a non-stem cell transforms into a different type of cell, or when an already differentiated stem cell creates cells outside its already established differentiation path. In accordance with the present disclosure, the mesanchymal stem stells (the neutralized ones) transdifferentiated into neurons, astrocytes and oligodendrocytes, each being obtained at statistically significant amounts.

As used herein, the term "mesenchymal stem cells" (MSC) denotes multipotent stromal stem cells that have the ability to differentiate into cells of the mesodermal lineage, such as adipocytes (fat cells), osteoblasts (bone cells) and chondrocytes (cartilage cells).

The term "multipotent" refers to stem cells which are capable of giving rise to many number of cell types.

The source of the MSC according to the present disclosure is not limited and may be derived from any appropriate biological source, for example from bone marrow, adipose tissue, umbilical cord tissue, umbilical cord blood and peripheral blood. The source may be human or non-human. In one embodiment, the MSC are human MSC.

In some embodiments, the MSC are obtained from bone marrow. The "bone marrow" (BM) refers to the flexible tissue found in the interior of bones.

In some embodiments, the MSC are not obtained from an adipose tissue.

In some further embodiments, the NMSC are not formed from adipose-derived stem cells.

The MSCs may be obtained from the BM by conventional methods such as aspiration or biopsy or any other method for providing MSCs. In BM aspiration a semi-liquid is obtained which may be further diluted with peripheral blood.

In some embodiments, the BM is harvested and the BM sample is treated to select the mesanchymal cells (also referred to as stromal cells). Selecting for BM mesanchymal/stromal cells may be in a number of ways. For example, stromal cells may be disaggregated and cultured inside a plastic container and then separated by their survival in specific media and adherence to the plastic.

The BM sample obtained from a subject may be stored under appropriate conditions prior to use for example the sample can be stored in liquid nitrogen after the separation of BM in mononuclear cells using, for example, Sepax separation method or may be used immediately after removal.

In some embodiments the BM may be obtained from a healthy donor. Alternatively, the BM may be obtained from a subject diagnosed with a disease, including, without being limited thereto, neurodegenerative diseases or inflammatory disorders, including autoimmune disorders. In some embodiments, the BM is obtained from a subject diagnosed with multiple sclerosis (MS).

As noted herein, the BM is a source of MSCs (stromal cells). The MSC may be identified by using five markers by FACS analysis for identification of the cells.

For example, the cells may be characterized by at least of the being negative for CD34 and CD45 and positive for CD73, CD105 and CD90. The term negative is used to note that no intensity or an intensity that is like the control intensity is observed in the FACS analysis. The term positive is used to note that a higher intensity than control is observed in the FACS analysis.

In accordance with the present disclosure, the MSCs are cultured in a culture medium that supports formation of MSC-derived NPs like structures from MSC which are referred to herein as "neutralized MSC".

As used herein the terms "neuralized MSC" or "NMSC" which are used herein interchangeably, refer to non-adherent (free-floating) spherical clusters of stem cells and progeny therefrom. The NMSC have a neurosphere-like structures characterized by the non-limiting markers, Nestin and PS-NCAM, which are characteristic antigens for neurospheres; the NMSC are further characterized by the capability to induce a dose-dependent suppression of lymphocytes proliferation. As such, while having a neurosphere structure, they are distinguished from classical neurospheres generated from adult neural stem cells (at least for the reason that they are produced from a different cell source).

The culture medium that supports formation of NMSC from MSCs at minimum comprises at least one growth factor. In addition, the culture medium comprises a serum free medium supplemented with a serum substitute. In some embodiments, the culture medium comprises at least two growth factors. This culture medium is referred to herein as the "first culture medium".

The first culture medium that supports formation of NMSC from MSC may include a variety of combinations of serum free media, serum substitutes and growth factors, as known in the art. For example and without being limited thereto, the first culture medium that supports the directed formation of NMSC comprises a basic serum free medium selected from the group consisting of Neurobasal™ (Gibco, Invitrogen cell culture, USA Cat. No. 21103-049 1998/1999), DMEM-F12 (Gibco, Invitrogen cell culture, USA Cat. No. 11320-033), Cellgro Stem Cell Growth Medium (Cat No. 2001 CellGenix Germany 2005), KO-DMEM (Cat. No, 10829-018 Gibco 1998/1999) and X-Vivo 10 (Cat. No. 04-380Q Lonza Switzerland 2007).

In some embodiments, the serum free medium is DMEM-F12. The serum free medium is DMEM-F12 typically comprises the following ingredients:

| COMPONENTS | Concentration (±5%) (mg/L) |
|---|---|
| INORGANIC SALTS | |
| Calcium chloride (CaCl2) | 116.70 |
| Cupric sulfate (CuSO4—5H2O) | 0.0013 |
| Ferric nitrate (Fe(NO3)3—9H20) | 0.05 |
| Ferrous sulfate (FeSO4—7H2O) | 0.417 |
| Potassium chloride (KCl) | 311.80 |
| Magnesium chloride (MgCl2) | 28.64 |
| Magnesium sulfate (MgSO4) | 48.84 |
| Sodium chloride (NaCl) | 6995.50 |
| Sodium bicarbonate (NaHCO3) | 1200 |
| Sodium phosphate, mono. (NaH2PO4—H20) | 62.50 |
| Sodium phosphate, dibas (Na2HPO4) | 71.02 |
| Zinc sulfate (ZnSO4—7H2O) | 0.432 |
| OTHER COMPOUNDS | |
| D-Glucose | 3151.00 |
| Hypoxanthine | 2.05 |
| Linoleic Acid | 0.042 |
| Lipoic Acid | 0.105 |
| Phenol red | 8.10 |
| Putrescine-2HCl | 0.081 |
| Sodium Pyruvate | 55.00 |
| HEPES | 3575.00 |
| Thymidine | 0.365 |
| AMINO ACIDS | |
| L-Alanine | 4.45 |
| L-Arginine hydrochloride | 147.50 |
| L-Asparagine-H2O | 7.50 |
| L-Aspartic acid | 6.65 |
| L-Cysteine-HCl—H2O | 17.56 |
| L-Cystine | 24.00 |
| L-Glutamic acid | 7.35 |
| Glycine | 18.75 |
| L-Histidine-HCl—H2O | 31.48 |
| L-Isoleucine | 54.47 |
| L-Leucine | 59.05 |
| L-Lysine hydrochloride | 91.25 |
| L-Methionine | 17.24 |
| L-Phenylalanine | 35.48 |
| L-Proline | 17.25 |
| L-Serine | 26.25 |
| L-Threonine | 53.45 |
| L-Tryptophan | 9.02 |
| L-Tyrosine | 38.70 |
| L-Valine | 52.85 |
| VITAMINS | |
| Biotin | 0.0035 |
| D-Calcium pantothenate | 2.24 |
| Choline chloride | 8.98 |
| Folic acid | 2.65 |
| i-Inositol | 12.60 |
| Niacinamide | 2.02 |
| Pyridoxal hydrochloride | 2.00 |
| Pyridoxine hydrochloride | 0.031 |

| COMPONENTS | Concentration (±5%) (mg/L) |
|---|---|
| Riboflavin | 0.219 |
| Thiamine hydrochloride | 2.17 |
| Vitamin B12 | 0.68 |

The culture medium may be further supplemented by components known to be used in culture, such as serum free supplement. In some other embodiments, the serum free supplement is B27.

The B27 components are provided below:
Components
  Biotin
  DL Alpha Tocopherol Acetate
  DL Alpha-Tocopherol
  Vitamin A (acetate)
  BSA, fatty acid free Fraction V
  Catalase
  Human Recombinant Insulin
  Human Transferrin
  Superoxide Dismutase
  Corticosterone
  D-Galactose
  Ethanolamine HCl
  Glutathione (reduced)
  L-Carnitine HCl
  Linoleic Acid
  Linolenic Acid
  Progesterone
  Putrescine 2HCl
  Sodium Selenite
  T3 (triodo-I-thyronine)

The first culture medium also included at least one growth factor, preferably, at least two growth factors, the growth factor(s) being capable of stimulating at least growth, and possible also proliferation and differentiation of the cells in the medium. In some embodiments, the growth factor is selected from the group consisting of Epidermal growth factor (EGF), Fibroblast growth factor (FGF), such as FGF-β (bFGF), Platelet-derived growth factor (PDGF), Transforming growth factor alpha (TGF-α), Transforming growth factor beta (TGF-β). In some embodiments, at least two growth factors are used. When using two growth factors, a preferred embodiment comprises the use of EGF and bFGF.

Figure 3:
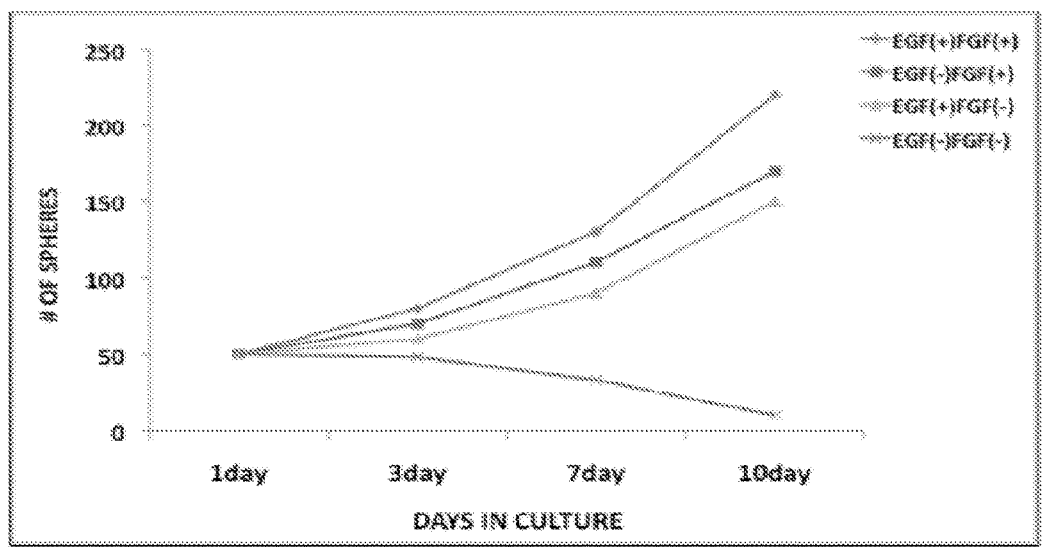
FIG. 3 is a graph showing survival and proliferation kinetics of NMSC, the best culture conditions for NMSC were found to be with the combination of the two growth factors EGF and FGF as a supplement for the culture media; loss of one of these growth factors resulted in halting the proliferation rate whereas loss of both of the growth factors resulted eventually in death and dissociation of the NMSC.

As shown in FIG. 3, the presence of growth factors enhances the formation of NMSC. Specifically, the NMSC proliferation and viability requires the presence of at least one of EGF and bFGF in the culture media. Absence of one of these particular factors results in decline of the proliferation and viability of the NMSC. Absence of both growth factors eventually resulted in the dissociation and death of the NMSC.

Accordingly, in some embodiments, the growth factor is at least one of EGF and bFGF. In some other embodiments, the growth factor is the combination of EGF and bFGF.

In some embodiments, EGF is human EGF, this includes, without being limited thereto, the 6045 Da EGF protein known in the art to promote cell growth.

In accordance with some embodiment, the formation of NP like structures is on plastic dishes (flasks). In some further embodiments, the cells are grown in flasks with minimal cell adhesion. This may be achieved by using ultra Low-Adherence™ flasks as known in the art. The use of such non-adherent growth environment allows the free floatation of the cells and formation of the non-adherent floating spheres.

The first culture media is preferably refreshed at least once and after several days. In one embodiment, the first culture media is replaced every 2-4 days and in yet some embodiments, at least once a week and even twice a week.

In accordance with some embodiments, the culture in the first culture media is for a time sufficient to allow the establishment/formation of the NMSC (exhibited by at least one of the markers characteristic of NMSC, e.g. Nestin and PS-NCAM and disappearance of the markers of their origin, i.e. the markers of MSC, as further discussed below).

As appreciated, the minimal time for the formation of NMSC from MSC will dependent, inter alia, on the conditions of culture but also on the original MSC culture and the density of the MSC. A person versed in the art will be able to determine the time sufficient for formation of NMSC, for example, by trial and error.

In some embodiments, formation of NMSC is observed after at least 24-48 hours. Notwithstanding this fact, at times, the NMSC are maintained in culture with the first culture media for more than 48 so as to maximize density of the NMSC in the culture and their stability. To this end, and in accordance with some embodiments, the NMSC are cultured in the first culture media for at least 2-10 days, preferably 4-7 days (with periodical replenishing) to obtain the desired quality and density of the NMSC. Accordingly, in some embodiments, the time sufficient for culturing in a first culture medial is between 2-10 days, at times, between 2 to 9 days, 3-8 days, 3-7 days and preferably between 4-7 days. Under these conditions, the culture is predominantly composed of a low but significant proportion (95%) of NMSC (less than 5% of MSC).

Once the modified culture (i.e. that containing predominantly NMSC) is obtained, namely there is evidence for the formation of neurosphere-like structures in the culture, the first culture medium is replaced at least once with a fresh amount of either the same first culture medium or modified version thereof which contains at least one growth factor and/or at least a serum free medium (this being regarded as the "renew culture medium"). In some embodiments, this culture medium being renewed comprises the same first culture medium, possibly serum free medium and growth factors and is lacking the serum substitute (e.g. B-27 supplement). In one embodiment, for proliferation and maintenance of the NMSC the medium comprises at least DMEM-F12, EGE and bFGF.

The inventors have found that in contrast to cultured MSC which express on their surface CD90 and CD105, more than 90% of the cells within a single neurosphere like structure (namely, within the NMSC) express Nestin and PS-NCAM, which are characteristic antigens for neutralized MSC.

The NMSC formation was thus characterized by low expression or lack of (negative, in scientific terms) a MSC marker selected from the group consisting of CD90, and CD105 and positive expression of a neurosphere marker selected from the group consisting of nestin and PSNCAM.

In addition, the inventors have found that the NMSC have immunomodulatory properties similar to the immunomodulatory properties of naïve MSCs as well of neural stem cells and were shown to induce a dose-dependent suppression of the proliferation of lymphocytes.

The NMSC are allowed to proliferation in the replaced (renew) growth medium. It should be noted that the time period for proliferation in the renewed medium is dependent inter alia on several factors for example the density of the NMSC, number of NMSC and viability of the NMSC.

In some embodiments, the time sufficient for further proliferation (e.g. in the renewed media) is between 1 day to 7 days, at times between 2 days to 6 days, at times even between 3 days to 4 days. After a suitable period of time of about 3 days or 4 days the NMSC can be further used.

Once desired NMSC are formed ("desired" meaning expressing at least the aforementioned markers and after the first culture medium is at least once replaced with a new volume of first culture medium), the culture medium may be replaced with a second culture medium comprising at least a serum free medium as defined above and cerebrospinal fluid (CSF). In some embodiments, the serum free medium comprises at least DMEM-F12 together with CSF.

When referring to CSF it is to be understood as meaning the clear colorless fluid produced in the brain and which may be collected from the spinal cord of either the subject that needs treatment, as further discussed below, or from a healthy donor, by any known technique, including, without being limited thereto, lumbar puncture. The amount of CSF may vary in the second culture medium and in some embodiments, the volume is between about 0.1% (v/v) to about 1% (v/v) CSF out of the total volume of the medium.

As noted above, the CSF may be "allogeneic or "autologous". In some embodiments, the CSF is an allogeneic CSF.

When referring to allogeneic CSF it is noted that the CSF provided to a recipient from a genetically non-identical donor. Namely, the CSF is obtained from a donor/patient and provided to a different person in need of the resulting neuronal cells. The CSF may be collected from donors who are either patients for example in the emergency room or at a treatment department or from donors per se.

When referring to autologous CSF it is noted that the CSF is obtained from and provided to the same patient.

Figures 4A, 4B:
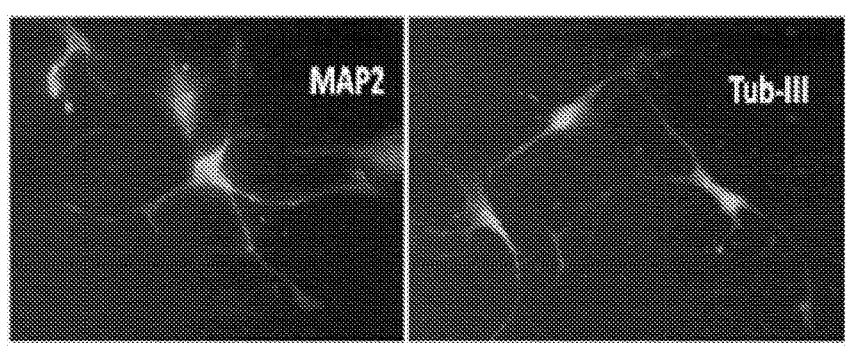
FIGS. 4A to 4J are images of neuronal cells.
Figures 4C, 4D:
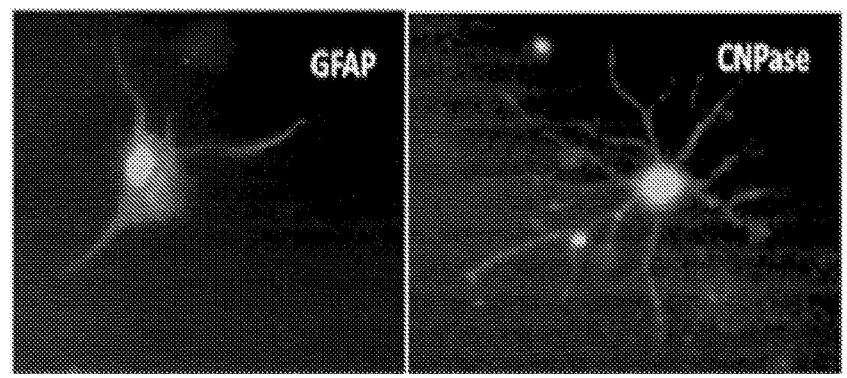

The second culture medium induces differentiation of the NMSC. Specifically, visual inspection and immunehistochemistry of specific markers, showed that the NMSC differentiate into cells of an ectoderm lineage including terminally differentiated astrocyte, neurons and oligodendrocyte. Specifically, as shown in FIG. 4A-4D, the inventors have found that differentiation induced by CSF resulted in the formation of Microtubule-associated protein 2 (MAP2)- and Class III β-tubulin (βIII-tubulin or β-tubulin III), positive cells with neuronal morphology (FIGS. 4A and 4B, respectively), Glial fibrillary acidic protein (GFAP)-positive cells with astrocyte morphology (FIG. 4C), and 2',3'-Cyclic-nucleotide 3'-phosphodiesterase (CNPase)-positive cells with oligodendrocyte morphology (FIG. 4D).

Figure 4E:
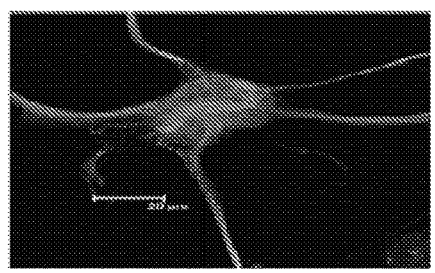

In general, astrocytes are "star-shaped" cells as shown in FIG. 4E. When referring to "astrocytes" for example in ex-vivo tissues or in-vitro isolated, it should be understood to refer to cells having both the matured astrocytes morphology (i.e. the star shape) and being positive for staining for GFAP. Cells showing only positive for staining for GFAP are not considered astrocytes.

In addition, it is known that naïve mesenchymal stem cells may hold a positive expression for GFAP (Foudah et al 2012, Blondheim et al 2006) even not in their differentiated state. Thus, morphological similarity for "star shaped" astrocytes is essential for defining astrocytes.

In some embodiments, the astrocytes according to the invention have a "star-shaped" like structures indicating their resemblance to astrocytes.

As shown in FIG. 4C, the cells show a clear "star-shaped" like structures and were positively stained with GFAP similarly to real astrocytes isolated from the brain (FIG. 4E, prior art).

Figures 4F, 4G:
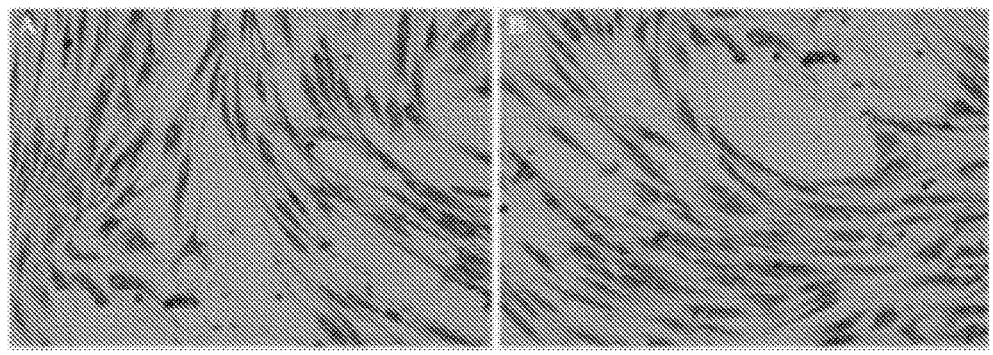
Figures 4H, 4I, 4J:
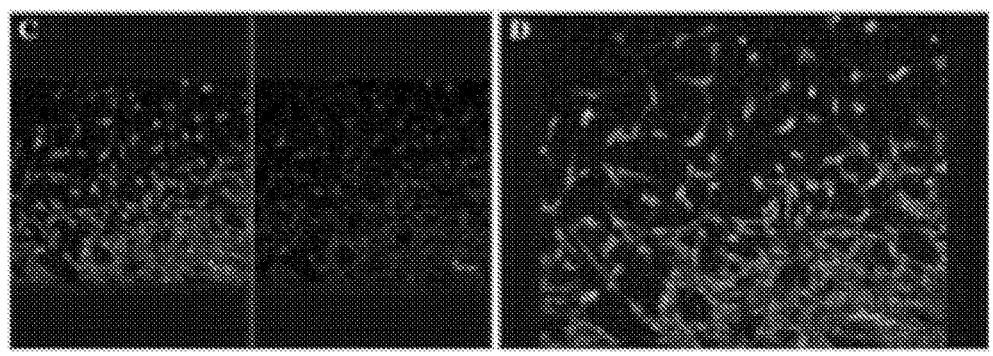

Thus, in some further embodiments, the differentiated NMSC have both the star shape and are positive for GFAP. This is supported, inter alia, by the following findings:

To compare with the cells of Ye et al., MSC were treated with CSF (as described in Ye et al. ibid.) to obtain "neuron like cells". FIGS. 4F to 4J, show that treatment of MSC with CSF resulted in cells which showed positive staining for GFAP and Class III β-tubulin, respectively. FIGS. 4F and 4G show immunohistochemistry staining of GFAP and Class III β-tubulin respectively and FIGS. 4H and 4I show immune-fluorescence staining of GFAP and Class III β-tubulin respectively.

However, the morphology of these cells did not resemble real neurons as no "star-shaped" like structures was observed. These cells conserved their elongated fibroblast-like shape that is identified with naïve MSC.

Table 2 shows that cells obtained by the method disclosed herein (i.e. after treatment of NMSC (and not MSC) with CSF) express MAP2, Tubulin-beta-III, GFAP, S100, GalC and CNPase as determined from staining of these markers. The cells obtained by the method disclosed herein showed at least a 10% expression of these markers.

For example, the cells obtained by the method disclosed herein showed at least a 10% expression of GFAP and Tubulin-beta-III, at times at least 20% expression, at times at least 30% expression, at times at least 40% expression, at times at least 50% expression, at times at least 60% expression, at times even at least 65% expression.

For example, the cells obtained by the method disclosed herein showed at least a 10% expression of MAP2 and S100, at times at least 20% expression, at times at least 30% expression, at times even at least 35% expression.

For example, the cells obtained by the method disclosed herein showed at least a 10% expression of GalC and CNPase, at times even at least 15% expression.

In connection with the present disclosure expression is determined from the ratio of the positively stained cells determined as detailed herein below. Staining may be obtained from any method known in the art such as but not limited to FACS, immunofluorescence.

In contrast, MSC treated directly with CSF (according to the method of Ye et al) showed reduced expression as compared to the cells obtained by the method disclosed herein (i.e. after treatment of NMSC (and not MSC) with CSF).

As shown in Table 2 the expression as determined from staining of the markers MAP2, Tubulin-beta-III, GFAP, S100, GalC and CNPas is increased in the cells obtained by the method disclosed herein (i.e. after treatment of NMSC (and not MSC) with CSF).

Specifically, positive staining of the "neuron-like cells" with GFAP and S100 was observed in the cells obtained by the method of Ye et al. However, staining of β-tubulin or MAP2 markers was hardly observed and no staining was detected for the oligodendrocytic markers GalC and CNPase.

Without being bound by theory, these results suggest that no oligodendrocytes are obtained by the method described by Ye et al.

Taken together, these results suggested that treatment of MSC directly with CSF and not via the a priori formation on NMSC, did not result in formation of neurons that need to exhibit an arsenal of features characterizing neurons and did not have the activity neurons.

On the other hand, the neurons derived from NMSC in accordance with the present disclosure shows the required features for defining the resulting cells as neurons. Specifically, the resulting NMSC derived cells showed staining of antigens and cell morphology which was identical to the staining and morphology observed in differentiated neurospheres derived from adult neural stem cells.

The resulting population of cells includes predominantly the mixture of astrocytes, neural cells and oligodendrocytes.

The term "comprising predominantly" is used to denote a population wherein at least 50%, at times 60%, at times even 90%, at times 95%, at time even 99% or even 100% of the cells exhibit characteristics of the above three cell types. The ratio between the cell types may vary.

In some embodiments, the ratio between the three cell types is 16:3:1 for neurons:astrocytes:oligodendrocytes. In some other embodiments, the population comprises about 80% neurons, about 15% astrocytes and about 5% oligodendrocytes.

In addition, if was found that the NMSC potential to differentiate into cells of a mesodermal lineage was lost including their ability to differentiate into adipocytes, osteoblasts, or chondrocytes (data not shown).

Further, it was found that the neuronal cells that differentiated from MSC not only express neuronal markers but importantly were also functional.

Specifically, as shown in Table 1 in the Examples the effect of differentiated NMSC on neurite length in N2A cells was superior over the non-differentiated NMSC or MSC and as good as the effect of the positive control used.

In addition, as shown in Table 3 neurite length in N2A cells at the cells obtained by the method of Ye et al, namely MSC treated with CSF, was lower compared to the cells obtained by the method developed herein.

In general, when cells differentiate in culture towards cells from the neuronal lineage, they secrete neurotrophic factors such as: Brain-derived neurotrophic factor (BDNF), Nerve growth factor (NGF), Ciliary neuronotrophic factor (CNTF) etc. Secretion of these factors is highly important in terms of neuroprotection and possible neuro-regeneration. As shown in Table 4, the population of cells obtained in accordance with the present disclosure secreted at least 5 times, 6 times, 7 times, 8 times, 9 times and even 10 times the amount of NGF as compared to naïve MSC, and at least 1.5 times, between 1.5 and 2 times or even essentially twice the amount of BDNF as compared to naïve MSC. In comparison, treatment of MSC with CSF (in accordance with the method of Ye et al.) resulted in secretion of much lower amounts of these growth factors, as shown in Table 4 (column "MSC induced with CSF").

Thus, in some embodiments, the population of cells secreted at least the above neurotrophic factors. In some other embodiments, the population of cells secreted at least BDNF and NFG.

It was thus suggested that the population of cells comprising terminally differentiated neurons, astrocytes and oligodendrocytes obtained as disclosed herein have neurotrophic effects and as such can promote protection and repair of neurodegenerative diseases.

In other words, it was concluded that culturing stable NMSC for at least 48 hours with CSF leads to a controlled path of differentiation favoring ectoderm lineage including terminally differentiated astrocyte, neurons and oligodendrocyte over mesodermal lineage.

Without being bound by theory, it was suggested by the inventors that formation of NMSC is a crucial step in affecting the differentiation route towards ectoderm lineage to thereby obtain the terminally differentiated astrocyte, neurons and oligodendrocyte are obtained.

Taken together, the results presented herein provide a cell population comprising terminally differentiated astrocyte, neurons and oligodendrocyte that is valuable for neuronal survival, neuronal growth and differentiation.

Once the population of cells is formed, they may used for various applications, both in research and in medicine. When referring to a population of cells it is to be understood as meaning a population comprising terminally differentiated astrocyte, neurons and oligodendrocyte.

Figure 6:
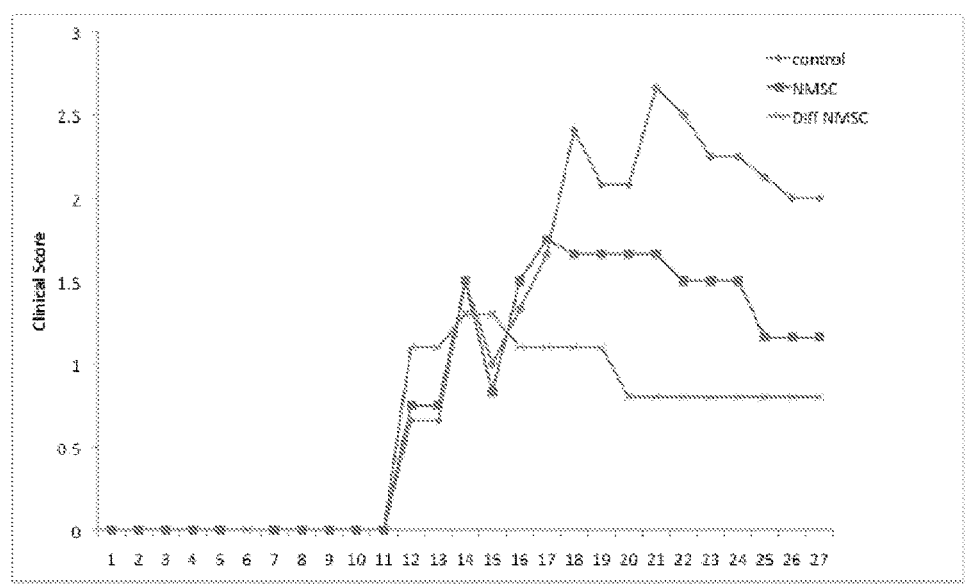
FIG. 6 is a graph showing the clinical score of chronic EAE in treated or non-treated EAE induced mice.

As shown in FIG. 6 in the Examples the effect of differentiated NMSC on clinical score of cEAE and animals mortality was superior over the non-differentiated NMSC or MSC.

In some aspects, the present disclosure provides use of MSC for the preparation of a composition comprising a population of cells comprising terminally differentiated neurons, astrocytes and oligodendrocytes.

In some other aspects, the present disclosure provides use of neutralized mesanchymal stem cells (NMSC) for the preparation of a population of cells comprising terminally differentiated neurons, astrocytes and oligodendrocytes.

In some embodiments, the NMSC according with the present disclosure may be characterized by low expression or lack of an MSC marker selected from the group consisting of CD90, and CD105 and expression of a neurosphere marker selected from the group consisting of nestin and PSNCAM. In some other embodiments, the population of cells may be characterized by expression of human microtubule-associated protein 2 (MAP-2) being characteristic of neurons, expression of Glial fibrillary acidic protein (GFAP) being characteristic of astrocytes, and expression of 2'3'-cyclic nucleotide 3'-phosphodiesterase (CNPase) being characteristic of oligodendrocytes. The population of cells may be characterized by secretion of neurotrophic growth factors at a level greater than their level from naïve mesenchymal stem cells. For example, the population of cells may be characterized by secretion of NGF or BDNF at a level greater than their level from naïve mesenchymal stem cells The composition described herein may be a pharmaceutical composition. The pharmaceutical composition optionally further comprise at least one pharmaceutically acceptable excipient or carrier. As used herein "pharmaceutically acceptable carrier" includes any and all solvents, dispersion media, coatings and the like. The use of such media and agents for pharmaceutical active substances is well known in the art.

In some embodiments, the pharmaceutical composition is for treating a pathological condition of the nervous system. In some other embodiments, the pharmaceutical composition is for treating a neurodegenerative disease or spinal cord injury. In yet some other embodiments, the use and pharmaceutical composition is for treating conditions that involve death of neurons and the treatment by the population of cells in accordance with the invention involves regeneration of neurons.

In the context of the present disclosure the term "Neurodegenerative diseases" is used to denote any condition that is characterized by progressive nervous system dysfunction and/or neuron cell death. There are more than 600 disorders afflict the nervous system. Neurodegenerative diseases may be associated with cognition, movement, strength, coordination, or myelin impairment, which are associated with the peripheral nervous system (PNS) or the autonomous nervous system (ANS).

In some embodiments the neurodegenerative disease may be one of but not limited to Parkinson's Disease (PD), Alzheimer's Disease (AD) and other dementias, Degenerative Nerve Diseases, Encephalitis, Epilepsy, Genetic Brain Disorders, Head and Brain Malformations, Hydrocephalus, Multiple Sclerosis, Amyotrophic Lateral Sclerosis (ALS or Lou Gehrig's Disease), Huntington's Disease (HD), Prion Diseases, Frontotemporal dementia, Dementia with Lewy bodies, Progressive supranuclear palsy, Corticobasal degeneration, Multiple system atrophy, Hereditary spastic paraparesis, Spinocerebellar atrophies, Amyloidoses, Motor neuron diseases (MND), Spinocerebellar ataxia (SCA), stroke and Spinal muscular atrophy (SMA).

In some embodiments, the neurodegenerative disease is multiple sclerosis (MS). Multiple Sclerosis, also known as disseminated sclerosis or encephalomyelitis disseminata, refers to an inflammatory disease in which myelin sheaths around axons of the brain and spinal cord are damaged, leading to loss of myelin and scarring.

In the context of this aspect, when referring to treating it may include inhibiting, preventing, ameliorating or delaying onset it is to be understood as meaning improvement of at least one characteristic of the disease such as: increase in disease free periods, decrease in acute disease periods or decrease in severity of the disease in the subject exhibiting at least the same disease characteristics.

The population of cells to the subject in need thereof may be self-administration as well as administration to the subject by another person.

The composition may comprise an amount of the population of cells that results in a medically statistically improvement of the subject's condition based on criteria acceptable for the particular condition being treated.

In some embodiments, the method involves administration by transplantation of the cell population into a subject's brain or cerebrospinal fluid.

The present disclosure provides in accordance with some further aspects, a kit comprising: (i) a composition comprising mesanchymal stem cells (MSC) (ii) instructions for use of the MSC in a method of preparing a population of cells comprising terminally differentiated neurons, astrocytes and oligodendrocytes, the method comprising: (a) culturing MSC in a first culture medium comprising a growth factor selected for allowing formation of neuralized MSC (NMSC); (b) allowing the NMSC to proliferate for a sufficient time during which said culture medium is renewed at least once; (c) culturing the NMSC of (b) in a second culture media comprising cerebrospinal fluid (CSF) for a time sufficient for the NMSC to differentiate into a population of cells comprising terminally differentiated neurons, astrocytes and oligodendrocytes.

All publications, patents and patent applications mentioned in this specification are herein incorporated in their entirety by reference into the specification.

As used in the specification and claims, the forms "a", "an" and "the" include singular as well as plural references unless the context clearly dictates otherwise. For example, the term "a stem cell" includes one or more stem cells and the term "stem cells" includes one stem cell as well as more than one stem cell.

As used herein, the term "or" means one or a combination of two or more of the listed choices.

Further, as used herein, the term "comprising" is intended to mean that the methods and culture systems includes the recited elements, but does not exclude others. Similarly, "consisting essentially of" is used to define methods and systems that include the recited elements but exclude other elements that may have an essential significance on the functionality of the culture systems of the inventions. For example, a culture system consisting essentially of a basic medium and medium supplements will not include or will include only insignificant amounts (amounts that will have an insignificant effect on the propagation of cells in the culture system) of other substances that have an effect on cells in a culture. Also, a system consisting essentially of the elements as defined herein would not exclude trace contaminants "Consisting of" shall mean excluding more than trace amounts of other elements. Embodiments defined by each of these transition terms are within the scope of this invention.

Further, all numerical values, e.g., concentration or dose or ranges thereof, are approximations which are varied (+) or (−) by up to 20%, at times by up to 10%, from the stated values. It is to be understood, even if not always explicitly stated that all numerical designations are preceded by the term "about". It also is to be understood, although not always explicitly stated, that the reagents described herein are merely exemplary and that equivalents of such are known in the art.

NON-LIMITING EXAMPLES

Materials and Methods
Bone Marrow Aspiration

Bone marrow aspiration was performed under short general anesthesia with puncture from the posterior superior iliac crest while the patient was lying in a left or a right lateral position. Approximately 200 mL of bone marrow inocula is usually obtained from each patient.
MSC Preparation and Culture A culture of purified MSCs was prepared under aseptic conditions (positively pressurized clean rooms) using filtered sterilized Dulbecco modified Eagle medium with low glucose levels (Qiagen, Valencia, Calif.) supplemented with 10% fetal bovine serum, 1% L-glutamine, and 1% penicillin-streptomycin-nystatin solution (all from Biological Industries, Kibbutz Beit-Haemek, Israel).

Mesenchymal cells were then cultured for 40 to 60 days, until they reached confluency, and were then harvested and cryo-preserved in 10% dimethyl sulfoxide-containing medium in liquid nitrogen (−196° C.). At 2 weeks, a sample was taken for sterility testing and quality control.
Generation and Propagation of Neutralized MSC (NMSC) from hMSC For the generation of NMSC, hMSC were cultured in ultra Low-Adherence™ flasks (Corning, Mexico) in DMEM-F12 serum free media (Biological Industries, Israel) containing 2% B-27 supplement (Gibco, USA), 20 ng/ml basic fibroblast growth factor (bFGF, Peprotech, Israel), 25 ng/ml epidermal growth factor (EGF, Peprotech, Israel), 1% non-essential amino acids (Biological Industries, Israel).

The cells were cultured for 14 days with medium exchange twice a week. Floating neurosphere-like structures (NMSC) were visible after 48 hours. The suspension was then washed gently by centrifugation and cells pellet was re-suspended in DMEM-F12 serum free media supplemented with 20 ng/ml bFGF, 25 ng/ml EGF, 5 µg/ml heparin, 1% non-essential amino acids and 1% MEM-alpha vitamins and seeded in ultra Low-Adherence™ flasks for propagation.
NMSC Differentiation Using Cerebrospinal Fluid (CSF)

To terminally differentiate NMSC into neural cell lineages, intact NMSC from passage 2 were used (namely, after the NMSC propagated at least once in the renew medium, i.e. the medium was at least once replenished). The NMSC from passage 2 were cultured in DMEM-F12/GlutaMax™ serum free medium (Invitrogen) supplemented with 1% non-essential vitamins (biological industries) and 0.2% autologous/allogenic CSF seeded in regular attachment tissue vessels (NUNC, USA).

Immunostaining of NMSC and Naive MSC

The medium was aspirated and the NMSC were washed gently with 0.03% Tween 20 (Sigma-Aldrich, Rehovot, Israel) diluted in DPBS and then fixed with fresh paraformaldehyde, 4%, for 20 minutes at room temperature. To stain the intracellular components, the cells were permeabilized with Triton X-100 (Sigma-Aldrich, Rehovot, Israel), 0.1%, for 10 minutes. For blocking nonspecific binding, the cells were rinsed with 2.5% bovine serum albumin in DPBS for 45 minutes at room temperature on a slowly rotating plate. Then, the cells were washed 3 times with 0.03% Tween 20 diluted in PBS, and incubated for 120 minutes with the following primary antibodies for mouse: anti human CD34, anti human CD45, anti human CD90, anti human CD105 anti human Nestin, anti human PS-NCAM, anti human MAP2, anti human GFAP, anti human MAP2 and anti human CNPase (all from Abcam, UK) diluted to the required concentrations with DPBS buffer containing 1% bovine serum albumin After washing, the cells were incubated with goat anti mouse fluorescein isothiocyanate-conjugated and goat anti rabbit tetramethylrhodamine isothiocyanate-conjugated secondary antibodies diluted in bovine serum albumin buffer, 1%, on a slowly rotating plate for 45 minutes in the dark at room temperature. The cells were mounted on slides with DAPI-mounting solution (Vectashield, Calif., USA) and examined under fluorescence and light microscopy. The number of immunoreactive cells was determined under a fluorescence microscope (Nikon, Japan) in relation to the nuclei stained with DAPI.

Proliferation Assay for NMSC (Immunological Potential Test)

NMSC growth was measured using the XTT based assay (Biological Industries, Israel). NMSC were seeded into 96 well plates at a density of 2000 NMSC/well and cultured for 3 days in the presence or absence of EGF (20 ng/ml, Peprotech, Israel), FGF-2 (25 ng/ml, Peprotech, Israel). After 3 days, 50 µl of MTT reaction solution was added to each well and plates were incubated at 37° C. for 2 hours. The absorbance of the samples against background ground control as blank was measured with ELISA reader (Beckman Coulter, USA) at a wavelength of 450-500 nm. In order to measure reference absorbance (for non-specific binding), a wavelength of 630-690 nm was used and subtracted from the 450-500 nm measurements. Within each experiment, absorbance at 590 nm values was averaged across 3 replicate wells.

Differentiation of N2A Cells (Neurotrophic Effects Model)

N2A cell were cultured in 24-wells plates (200 cells/well) in culture medium containing DMEM (high glucose formulation), 5% FBS and 1% penicillin-streptomycin (all from Biological Industries, Kibbutz Beit-Haemek, Israel). Differentiation was initiated in cultures confluent at a degree of 25-50%. Conditioned medium from naïve-MSC, NMSC and terminally differentiated cells were added to the cultured N2A cells for 3 days. To detect neurite outgrowth, cultured cells were immunostained with the neuronal marker MAP2 (Abcam®, Cambridge, UK). To measure neurites after differentiation the computerized analysis software ImageJ was used and the neurite length was calculated in pixels.

MSCs Treatment by Cerebrospinal Fluid (CSF)

The following protocol was adopted from Ye et al for comparative study. Briefly, for differentiation into neuronal-like cells, bone marrow stromal cells from two healthy volunteers were, respectively, plated at $2 \times 10^6$ cell/well (0.1 ml) on poly-1-lysine coated (100 mg/ml Sigma) coverslips in six-well plate. When cells grew to 70% confluence, cells were cultured with 10 µl of auto-CSF supplemented to the culture medium every day for 7 days.

Characterization of Cells after Treatment by Cerebrospinal Fluid (CSF)

The CSF treated NMSCs were further analyzed by studying additional parameters such as: Staining for the markers MAP2 (neuronal), S100 (Astrocytic) and GalC and CNPase (Oligodenrocyic), Computerized evaluation of the neurites length and Growth factors secretion by the differentiated cells. The results were compared to the result obtained by the method of the present invention.

In Vivo Studies

Naïve MSC were isolated from bone marrow of multiple sclerosis patients as described above. These cells were induced to form floating neruosphere-like structure (NMSC). Following NMSC generation (as described above) the cells were exposed to neuronal differentiation protocol using allogenic CSF to obtain differentiated NMSC as described above. Chronic Experimental Autoimmune Encephalomyelitis (cEAE) was induced with $MOG_{35-55}$ peptide in female C57BL/6 mice. On day 8 after EAE induction, the NMSC or the differentiated NMSC were injected intraventricularly into the cEAE induced mice. The mice were scored daily for neurological symptoms according to the EAE clinical severity scale (0=asymptomatic; 1=partial loss of tail tonicity; 2=tail paralysis; 3=hind limb weakness; 4=hind limb paralysis; 5=4-limb paralysis; 6=death).

In a further study with MOG-induced EAE in C57bl/6 mice, are intracerebroventriculary (ICV) injected on day 8 (following induction) in accordance with one of the following treatment groups:

(1) EAE non-treated animals (n=8)
(2) EAE injected with naïve MSC (n=8)
(3) EAE injected with MSC exposed to CSF (n=10)
(4) EAE injected with NMSC (n=8)
(5) EAE injected NMSC exposed to CSF (n=10)

During the 30 days from induction, the animals are evaluated by EAE clinical scores and histopathological parameters (inflammation and axonal loss).

Results

Derivation of NMSC from BM-MSC

To generate NMSC, MSCs (of passage 2-3, FIG. 1A) were trypsinized, collected, and cultured NMSC induction media containing DMEM-F12 serum free media supplemented with B27 supplement, epidermal growth factor (EGF) and basic fibroblast growth factor (basic FGF). Under these culture conditions cells started to form spheres (the NMSC) after 2 day of culture (FIGS. 1B and 1C).

Characterization of NMSC

To determine if the NMSC derived from MSCs resembled neurospheres, it was studied whether these spheres expressed two characteristic antigens for neurospheres, Nestin and PS-NCAM.

Figures 2A, 2B, 2C, 2D:
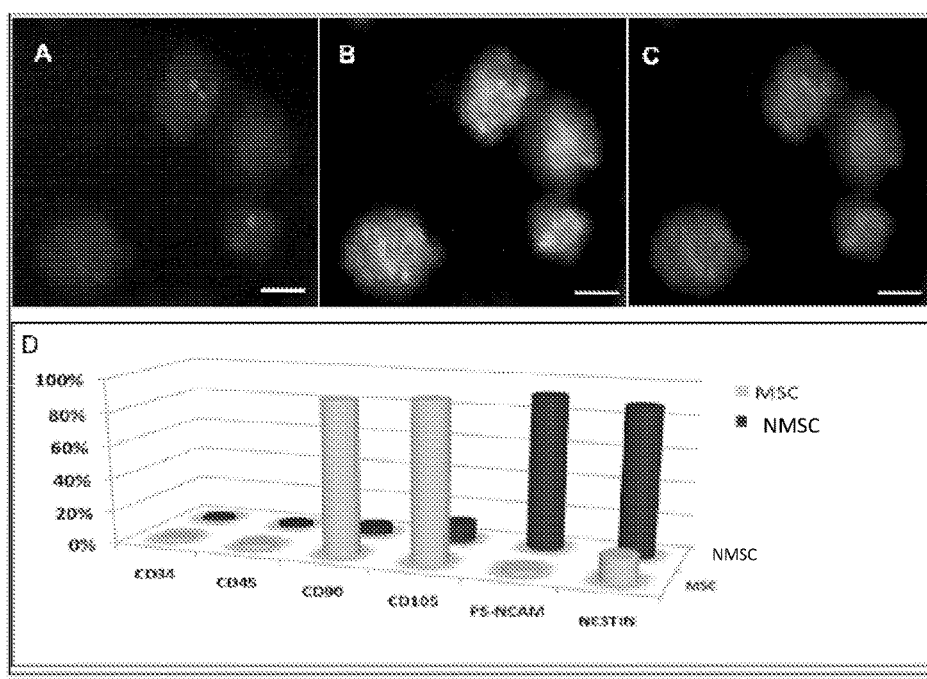
FIGS. 2A to 2D show characterization of NMSC.

Immunocytochemistry revealed that most of the cells (>90%) within a single sphere express Nestin and PS-NCAM (FIGS. 2A and 2B respectively, and FIG. 2C). In addition, it was investigated whether these MSC-NPs express antigens that are characteristic of MSCs. FACS analysis showed that these MSC-derived spheres did not express CD34, CD45 but did weakly express CD105(~5%), and CD90(~10%) (FIG. 2D).

Proliferation and Expansion of NMSC

In order to evaluate the proliferation rates and factors affect the growth kinetics in vitro the XTT-based assay was used. In these experiments, the essentiality of the epidermal and basic growth factors was evaluated. It was found that MSC-NPs proliferation and viability requires the presence of both growth factors EGF and bFGF in the culture media (FIG. 3). Absence of one of the factors results in decline of the proliferation and viability of the NMSC. Absence of both growth factors eventually resulted in the dissociation and death of the NMSC.

Neural Differentiation of NMSC

NMSC were cultured for differentiation as described in methods. Fluorescence immunocytochemistry for neuronal (MAP2) and glial cell antigens (GFAP and CNPase) was performed for MSC-NPs cultured for 7 days under differentiation conditions. MSC-NPs were able to differentiate into GFAP-positive cells with astrocyte morphology, MAP2-positive cells with neuronal morphology, and CNPase-positive cells with oligodendrocyte morphology (FIGS. 4A to 4D). When analyzed for their potential to differentiate into cells of a mesodermal lineage, it was found that these MSC-NPs have lost their ability to differentiate into adipocytes, osteoblasts, or chondrocytes (data not shown).

NMSC Suppress Lymphocytes Proliferation In Vitro

Figure 5:
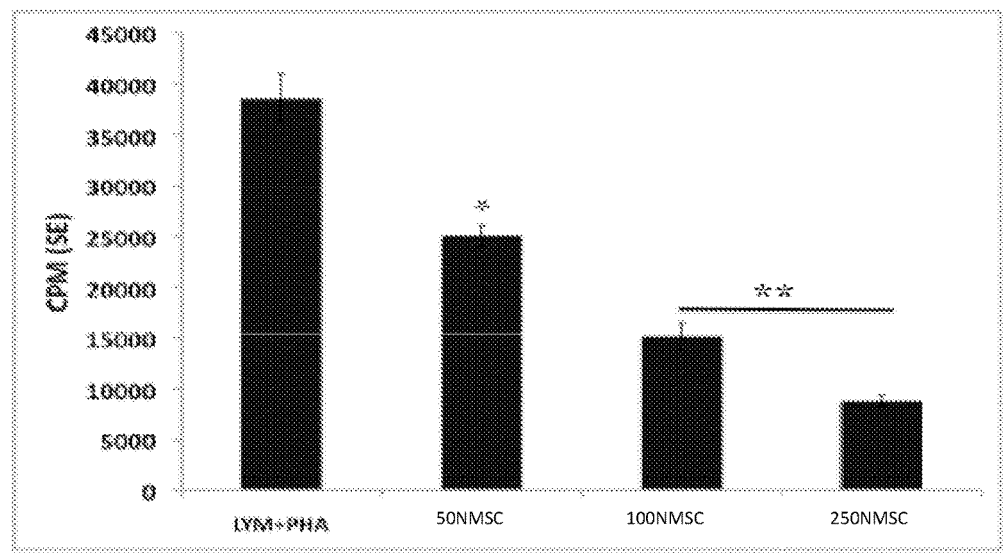
FIG. 5 is a bar graph showing that NMSC suppress lymphocytes proliferation; a significant dose dependent suppression of the proliferation of lymphocytes obtained from peripheral blood of healthy donor by NMSC was observed using a 3H-Thymidine incorporation assay (*p<0.05, **p<0.001).

To explore the capacity of NMSC to inhibit the proliferation of lymphocytes isolated from peripheral blood donation, naïve NMSC at different doses (50, 100 and 250 spheres) were co-cultured with lymphocytes at the presence of the mitogen PHA. The proliferation was measured using the $^3$H-incorporation assay after 3 days of co-culture. As shown in FIG. 5, The NMSC were found to inhibit the lymphocytes proliferations in a dose-dependent manner, similarly to the inhibitory effect observed by naïve MSC (Kassis et al., 2008) and NSC (Einstein et al., 2007). Further, the NMSC were shown to have greater similarity to classical neurospheres derived from adult NSC.

In addition, as shown in Table 4, the cells treated with CSF secreted neurotrophic factors such as: BDNF, NGF. These factors are known to be of high importance in terms of neuroprotection and possible neuro-regeneration and suggest the clinical use of the cells obtained by the method of the present invention.

NMSC and Terminally Differentiated Cells have Neurotrophic Effects In Vitro

Evaluation of the neurotrophic effects of NMSC and cells differentiated from the NMSC was studied in the N2A cell system.

In normal conditions, N2A cells undergo neural differentiation after exposure to retinoic acid or serum withdrawal. N2A cells were cultured with conditioned media from NMSC and cells differentiated from NMSC (collected after 72 hours of culture). The effects of the supernatant on neurite outgrowth of the N2A were visualized by immunostaining with the neuronal marker MAP2 and neurites length was calculated by the ImageJ Software.

Positive staining for the neuronal marker MAP2 was detected after culturing for 72 hours with the supernatant of cells from all cell types (not shown). As shown in Table 1, the length of the generated neurites was 85±10.7 and 127±20.43 pixels/neurite (calculating 20 cells, 150 neurites) following culture with supernatant from NMSC and the differentiated NMSC respectively, (p>0.1).

TABLE 1

| Neurite outgrowth | | | |
|---|---|---|---|
| Control | MSC | MSC-NPs | Diff MSC-NPs (induced with CSF) |
| 198 ± 32.2 | 57 ± 12.3 | 85 ± 10.7 | 127 ± 20.43 |

As a positive control, N2A were cultured with 20 μM retinoic acid. The differentiated cells showed positive staining for the neuronal marker MAP2. The neurite length measurement of the retinoic acid differentiated cells was 198±32.2 pixels/neurite meaning that the differentiated MSC-NP are as almost good as the positive control indicating that NMSC hold a very powerful neurotrophic effect.

Comparative Study:

The following describes the differences in the morphology of the cells obtained in the method according to the present invention vs. the cells obtained by the method described by Ye et al. In addition, characterization of the cells obtained by the method described by Ye et al is presented.

As shown below, the results show that the cells obtained by the method of Ye et al do not differentiate to form oligodendrocytes and are not active as the cells according to the present invention.

MSC by grown using the protocol used by Ye et al and treated with CSF also showed a positive staining Class III β-tubulin. However, in contrast to the above, MSC by grown using the protocol used by Ye et al and treated with CSF, does not resemble the morphology of astrocytes isolated from the brain (FIGS. 4F-4I). This is in contrast to the cells obtained by the method described herein, which have a "star-shaped" like structures and astrocytes isolated from the brain (FIG. 4C).

The cells obtained by the method of Ye et al were compared to the cells obtained by the method of the present invention. The results are summarized in Table 2.

TABLE 2

| Ratio of the positive stained cells | | | |
|---|---|---|---|
| Marker | Cell Type (marker) | MSC induced with CSF (Ye et al)* | NMSC induced with CSF* |
| MAP2 | Neurons | 0-5% | 75-85% |
| Tubulin-beta-III | Neurons | 0-3% | 68-77% |
| GFAP | Astrocytes | 5-10% | 45-55% |
| S100 | Astrocytes | 5-8% | 35-45% |
| GalC | Oligodendrocytes | 0% | 15-20% |
| CNPase | Oligodendrocytes | 0% | 10-18% |

*% positive cells, replicates of 5 wells.

As can be seen in Table 2, in the cells obtained by the method of Ye et al, low positive staining of neuron-like cells with the markers Tub-beta-III or MAP2 was observed. Some of the cells indeed expressed positive staining for the astrocytic markers GFAP and S100.

In addition, no positive staining was detected for the oligodendrocytic markers GalC and CNPase. Further, to the morphological results showing that the CSF-treated cells conserved their elongated fibroblast-like shape that is identified with naïve MSC, the results suggest that treatment of MSC with CSF is not sufficient to induce differentiation as obtained by the method of the present invention.

To detect neurite outgrowth, cultured cells were immunostained with the neuronal marker MAP2. To measure neurites after differentiation the computerized analysis software Image) was used and the neurite length was calculated in pixels. The results are shown in Table 3:

TABLE 3

| Neurite outgrowth | |
|---|---|
| MSC induced with CSF* | NMSC induced with CSF* |
| 37 ± 8 pixels/neurite | 118 ± 12 pixels/neurite |

*pixels ± SD, calculation of 150 neurites

TABLE 4

| Growth factor secretion | | | |
|---|---|---|---|
| Factor ($O.D_{405\ nm}$) | Naïve MSC | MSC induced with CSF | NMSC induced with CSF |
| NGF | 0.2 ± 0.35* | 0.8 ± 0.09* | 2.7 ± 1.3* |
| BDNF | 1.4 ± 0.7* | 1.7 ± 0.4* | 3.3 ± 0.9* |

*Triplicates

As shown in Table 4, the cells obtained by the method of Ye et al secrete low amounts of neurotrophic factors (BDNF, NGF) compared to the cells obtained by the method described herein.

NMSC Attenuated Chronic Experimental Autoimmune Encephalomyelitis (cEAE) In Vivo As shown in FIG. 6, while NMSC attenuated disease severity after transplantation, differentiated NMSC provided significantly higher clinical scores. Specifically, the clinical course of cEAE was improved in NMSC treated animals (n=8), with 0% mortality and mean maximal EAE score 1.75 vs. 33% mortality and 3.33 mean maximal score in non-treated animals (n=10). Moreover, using differentiated NMSC (n=7) the effect was more superior with 0% mortality and mean maximal EAE score of 0.6 vs. 1.75 of NMSC and 3.33 of untreated animals.

The invention claimed is:

1. A method of inducing transdifferentiation of mesenchymal stem cells (MSC), the method comprising:
    a. culturing MSC in a first culture medium comprising a growth factor selected for allowing formation of neuralized MSC (NMSC), said growth factor comprising epidermal growth factor (EGF) and basic fibroblast growth factor (bFGF), and said NMSC being characterized by expression of Nestin;
    b. allowing the NMSC to proliferate for a sufficient time during which said first culture medium is renewed at least once;
    c. culturing the NMSC of (b) in a second culture medium comprising cerebrospinal fluid (CSF) for a time sufficient for the NMSC to differentiate into a population of cells including terminally differentiated neurons, astrocytes and oligodendrocytes, said population of cells is characterized by at least 10% expression [5] of Glial fibrillary acidic protein (GFAP) and Tubulin-beta-III, at least 10% expression of Microtubule-associated protein-2 (MAP-2) and S100 and at least a 10% expression of Galactosylceramidase (GalC) and 2' 3'-cyclic nucleotide 3'-phosphodiesterase (CNPase).

2. The method of claim 1, wherein said MSC are obtained from a healthy donor or from a subject being diagnosed with multiple sclerosis (MS).

3. The method of claim 2, wherein said MSC are obtained by bone marrow aspiration.

4. The method of claim 1, wherein said first culture media comprises a serum free medium supplemented with a serum substitute.

5. The method of claim 1, including renewing the first culture medium at least once a week.

6. The method of claim 5, including renewing the first culture medium at least twice a week.

7. The method of claim 1, wherein said CSF is an allogenic CSF.

8. The method of claim 1, including determining NMSC formation by low expression or lack of a MSC marker selected from the group consisting of CD90, and CD105 and expression of a neurosphere marker selected from the group consisting of nestin and polysialylated neural cell adhesion molecule (PSNCAM).

9. The method of claim 1, including determining formation of said population of cells by determining level of expression of human microtubule-associated protein 2 (MAP-2) being characteristic of neurons, expression of Glial fibrillary acidic protein (GFAP) being characteristic of astrocytes, and expression of 2'3'-cyclic nucleotide 3'-phosphodiesterase (CNPase) being characteristic of oligodendrocytes.

10. The method of claim 1, including determining for said population of cells level of neurotrophic growth factors being at a level greater than their level from nave mesenchymal stem cells.

11. The method of claim 10, wherein said neurotrophic growth factor is Nerve growth factor (NGF) or Brain-derived neurotrophic factor (BDNF).

12. The method of claim 1, wherein said population is characterized by at least 65% expression of GFAP and Tubulin-beta-III, at least 35% expression of MAP-2 and S100, and at least 10% expression of GalC and CNPase.

13. The method of claim 1, wherein said population is characterized by expression of MAP2 in an amount of 75-85%, Tubulin-beta-III in an amount of 68-77%, GFAP in an amount of 45-55%, S100 in an amount of 35-45%, GalC in an amount of 15-20% and CNPase in an amount of 10-18%.

* * * * *